United States Patent [19]

Bodnar

[11] Patent Number: 5,621,671
[45] Date of Patent: Apr. 15, 1997

[54] DIGITAL SIMULATION OF ORGANISMAL GROWTH

[75] Inventor: John W. Bodnar, Annapolis, Md.

[73] Assignee: The United States of America as represented by the Secretary of the Navy, Washington, D.C.

[21] Appl. No.: 405,638

[22] Filed: Mar. 17, 1995

[51] Int. Cl.$^6$ .................................................. G06F 19/00
[52] U.S. Cl. ........................................... 364/578; 364/496
[58] Field of Search ..................................... 364/578, 496

[56] References Cited

U.S. PATENT DOCUMENTS

| | | | |
|---|---|---|---|
| 4,855,931 | 8/1989 | Saunders | 364/499 |
| 5,025,388 | 6/1991 | Cramer, III et al. | 364/496 |
| 5,290,701 | 3/1994 | Wilkins | 435/312 |
| 5,342,401 | 8/1994 | Spano et al. | 607/5 |

OTHER PUBLICATIONS

"Achieving Von Neumann's Dream: Artificial Life on Silicon" P. Marchal et al., IEEE 1994, pp. 2321–2326.

*Primary Examiner*—Kevin J. Teska
*Assistant Examiner*—Andrew S. Roberts
*Attorney, Agent, or Firm*—John Forrest; Jacob Shuster

[57] ABSTRACT

The growth and development of a biological organism reflected as a series of molecular and cellular processes by chromatin switching networks, form threshold mechanisms applied through simulation transcription rules to pattern formations of a digital approximation of regulator concentration gradient. Digital logic statements are derived from such pattern formations to simulate the growth and development of the organism.

16 Claims, 4 Drawing Sheets

CELL CYCLES

ACTIVATOR

REPRESSOR

DIGITAL SIMULATION OF ORGANISMAL GROWTH

BACKGROUND OF THE INVENTION

This invention relates in general to a method of describing by digital approximation relatively complex growth and development of a biological organism.

Biological organisms such as Drosophilia develop from a fertilized egg undergoing a series of molecular and cellular processes based on DNA-stored programming information. Decoding of such programming information from which the growth and development process may be simulated, depends on biochemical events and mechanisms currently defined by chemical models. As such, current simulation methods rely heavily on the solution of differential equations. Computer approximations for simultaneous solution of such differential equations involve robust mathematical algorithms and a considerable amount of computer memory and time.

It is therefore an important object of the present invention to provide for simpler, more efficient and more rapid simulation of the relatively complex developmental processes associated with biological organisms by a method which may be practiced through programming of a low-cost personal computer.

In accordance with the foregoing object, it is an additional object of the present invention to provide a better conceptual simulation method for understanding the growth and development of a biological organism, as a more widely accessible tool for both research and educational purposes.

SUMMARY OF THE INVENTION

In accordance with the present invention, the processes involved in the growth and development of a biological organism are approximated by means of a digital switching network based on various factors, involving chromatin structures of genes and biochemical regulatory molecules switched under control of threshold mechanisms pursuant to Boolean logic rules. Based on the foregoing digital switching network, a series of digital logic statements are obtained for integration into a program from which the growth and development processes may be simulated. Such logic statements form the basis of the simulation program describing molecular and cellular processes, cell cycle linkages between recurring processes and between inputs and outputs of cell cycles in terms of regulator concentration, patterns of digital gradients and program changes under Boolean logic rules.

BRIEF DESCRIPTION OF DRAWING FIGURES

A more complete appreciation of the invention and many of its attendant advantages will be readily appreciated as the same becomes better understood by reference to the following detailed description when considered in connection with the accompanying drawing wherein.

DETAILED DESCRIPTION OF PREFERRED EMBODIMENTS

The method of the present invention while applicable to different kinds of organisms, is hereinafter described by example with regard to simulation of a most intensely studied biological system, involving development of an embryo of a biological organism 10, depicted in FIG. 1 as a blastula or blastoderm after completion of cleavage and formation therein of a cavity 12 bounded by a single layer of cells 14. Such organism is the genus of a fruit or pomace fly with respect to which Drosophilia embryogenesis or blastoderm is generally deemed to involve mechanisms that are almost exclusively position-dependent.

Figure 2A:
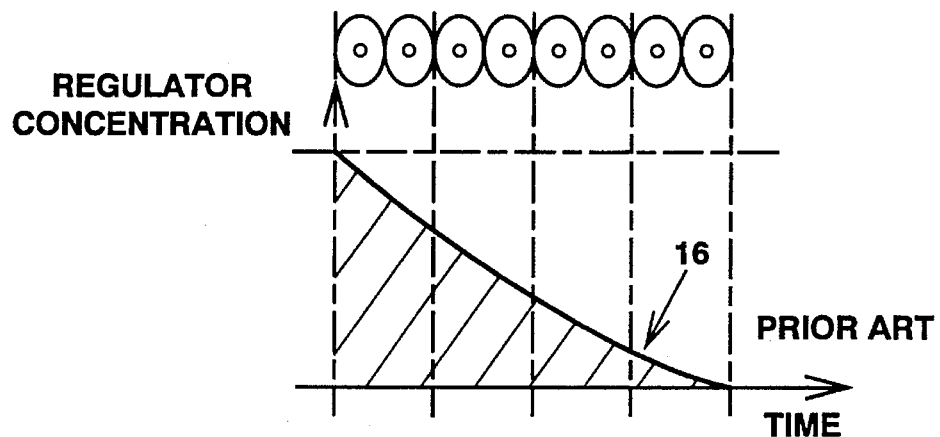
FIG. 2A is a graphical diagram of protein concentration in an embryo during growth and development.
Figure 2B:
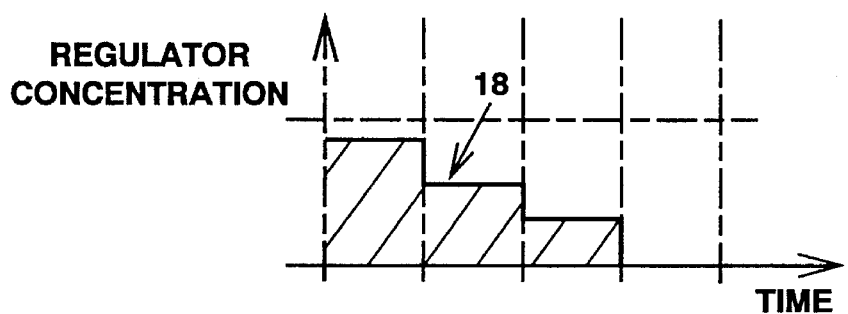
FIG. 2B is a graphical diagram of a digital approximation of the concentration gradient shown in FIG. 2A.
Figure 3:
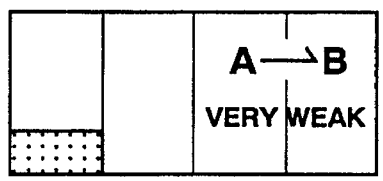
FIG. 3 is a diagram of simulated gene activation for embryonic development.
Figure 3:
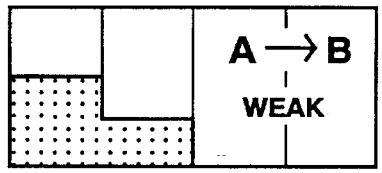
Figure 3:
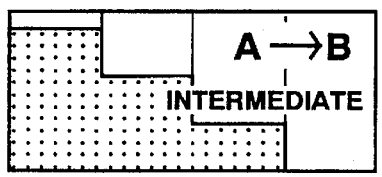
Figure 3:
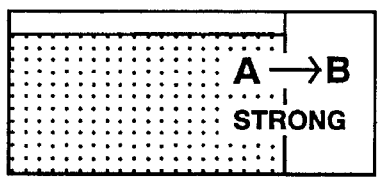
Figure 3:
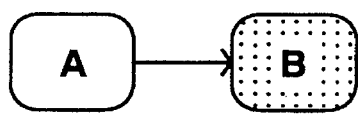
Figure 4:
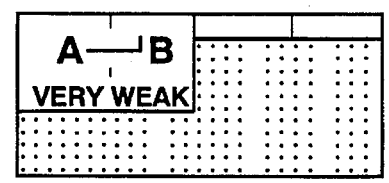
FIG. 4 is a diagram of simulated gene repression for embryonic development.
Figure 4:
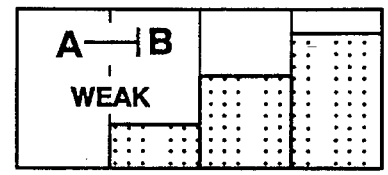
Figure 4:
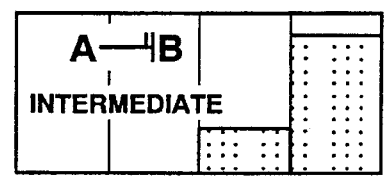
Figure 4:
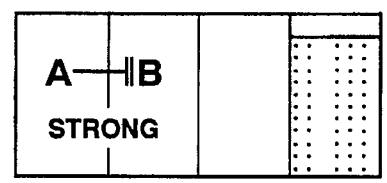
Figure 4:
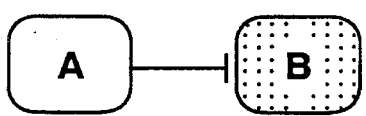

Two generic threshold mechanisms applicable to the Drosophilia blastoderm type of growth and development process are utilized to define formation of cell patterns in the embryo 10. Since such threshold mechanisms recur in many different organisms, they are of interest as models of chromatin switching integrated with models of positional information, pursuant to the present invention, for programmed simulation purposes. The chromatin switching is applicable to an approximation for the process of transformation of a target gene from an inactive state toward an active state at certain threshold concentrations of a biochemical regulator, such as a transactivator, hormone, oncogene, signal transducer, growth regulator or morphogen. One of the foregoing referred to threshold mechanisms involves a transactivator as the biochemical regulator found on the organism 10 shown in FIG. 1, having a chromatin switching threshold through which positional information is obtained for pattern formation simulation. Such threshold for a target gene is obtained from input data in the form of a continuously varying analog type of protein concentration gradient 16 show in FIG. 2A. Such input data gradient 16 is digitally approximated by biochemical analog-to-digital conversion into a step gradient 18 as shown in FIG. 2B, in order to digitally simulate chromatin switching. Thus, discrete digital signals for switching of genes between active and inactive states of the cells 14 in the organism 10, dependent on position in the gradient 18, reflect regulation of target genes. Each of the four steps of the gradient 18 as shown in FIG. 2B corresponds to a regulatory threshold, wherein input gene concentration determines target gene concentration on the next cell cycle by either activation or repression. Activator and Repressor actions are respectively depicted in FIGS. 3 and 4 as simulated pattern formations involving input gene A and target gene B. Activation varies in degree between the four gradient step levels as very weak ($\rightharpoonup$), weak ($\rightarrow$), intermediate ($\twoheadrightarrow$) and strong ($\twoheadrightarrow$) as depicted in FIG. 3. Correspondingly, repression also varies in degree between multiple gradient step levels, symbolized in FIG. 4 as (⇁), (⇀), (⇁ₕ) and (⇀ₕ).

The foregoing simulations are utilized to depict chromatin switching of gene activation and repression during different cell cycle phases in a developing embryo, as a simple digital network to which transcription rules are applied utilizing Boolean logic. Thus, threshold activation or repression associated with four different classes of genes A, B, C and D under Boolean simulation transcription rules, is summarized in the following table in terms of four values 0, 1, 2 and 3 of possible state of the cell protein concentration values.

| TYPE OF REGULATION | | PROTEIN OR REGULATOR STATES OF TARGET CELL | | | |
|---|---|---|---|---|---|
| | | NO PROTEIN PRESENT | CONCENTRATION THRESHOLD INPUT VALUES | | |
| | | | LOW | INTERMEDIATE | HIGH |
| values of input Regulator | | 0 | 1 | 2 | 3 |
| ACTIVATOR | very weak | X | X | X | 1 |
| | weak | X | X | 1 | 2 |
| | intermed. | X | 1 | 2 | 3 |
| | strong | X | 3 | 3 | 3 |
| REPRESSOR | very weak | X | X | 2 | 1 |
| | weak | X | 2 | 1 | 0 |
| | intermed | X | 1 | 0 | 0 |
| | strong | X | 0 | 0 | 0 |

From the foregoing table, it will be apparent that: a) each of the activators always gives a return value, b) repressors have no effect (X) if their value is already less than the return value and c) each rule overrides any other rule thereabove in the table.

Figure 5:
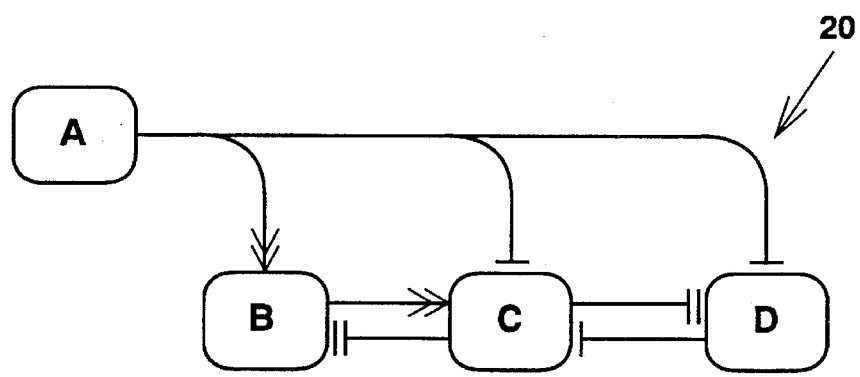
FIG. 5 illustrates a chromatin switching network pursuant to one generic threshold mechanism associated with growth and development of the embryo shown in FIG. 1.

Based on the foregoing table, FIG. 5 diagrams gene regulation in accordance with one of the two generic threshold mechanisms for chromatin switching simulation, in terms of interactions between the four classes of genes A, B, C and D aforementioned. As shown in FIG. 5, a single input gene A of the threshold mechanism forms a reproducible three stripe pattern of step gradients with the three other target genes B, C and D to form an activation-repression network 20. Starting with the input gene A, sequential activation is programmed to proceed to genes B and C. Feedback from the target genes C and D is inhibited to define a downstream border between genes C and D and upstream borders between gene A and genes B and C. Such programming requires three cell cycles during which gene concentrations are determined from current positional values 0, 1, 2 and 3 of the genes A, B, C and D, based on the Boolean logic rules as previously outlined in the table presented herein.

Figure 6:
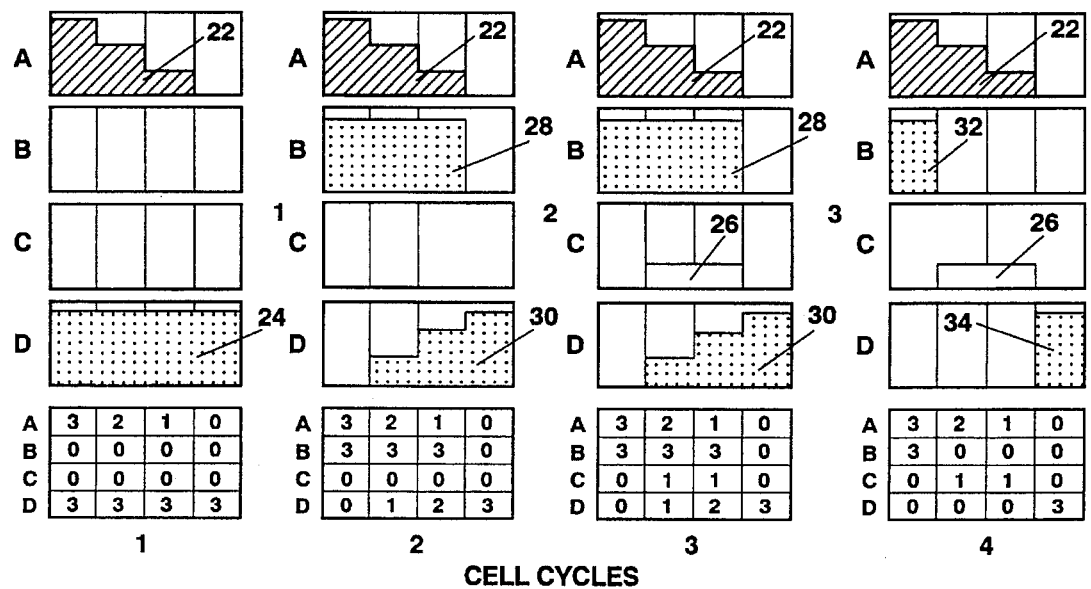
FIG. 6 illustrates digital simulation of growth and development corresponding to the switching network depicted in FIG. 5.

FIG. 6 diagrams formation of the programmed development pattern produced by the gene regulation network 20 depicted in FIG. 5 representing simulation of Drosophilia blastoderm. The concentration of input gene A in the egg 10, is represented in FIG. 6 by a step gradient 22 divided into three threshold levels during each of four growth phases corresponding to four compartments having different positional values. During the first growth phase or starting cell cycle, the positional values for the genes A, B, C and D are respectively (3210), (0000), (0000) and (3333) corresponding to the gradient concentrations 22 and 24 of genes A and D to reflect competition with chromatin and each other on the DNA of genes B, C and D as the target genes. Any nuclei in a given compartment, senses the local protein concentration and switches the chromatin of all target genes B, C and D in accordance with the Boolean transcription rules hereinbefore referred to.

During the second cell cycle, interactions occur amongst the target genes B, C and D while target gene B remains activated by input gene A. Gene C is activated as a target of gene B but is inhibited by feedforward repression of gene A, while the activation levels of gene C are limited by gene A and D. The gradient 30 of gene D is maintained by autoregulatory activation thereof and continued feedforward repression by gene A. The simulation of such second cycle shown in FIG. 6, corresponds to the positonal values of (3210), (3330), (0000) and (0123) for genes A, B, C and D respectively.

During the third cell cycle, a repressor accumulation gradient 26 of gene C is sharpened to abolish any affect on step gradients 28 and 30 of genes B and D, as a result of feedback and feedforward inhibition. After such third cycle, step gradient 32 of gene B is formed and maintained in the first compartment during the fourth cycle by autoregulatory activation, while genes B and D are repressed by gene C. Autoregulatory activation however maintains the step gradient 34 of gene D in the fourth compartment while it inhibits any new transcription of gene B or C. The third cell cycle is accordingly simulated by the positional values (3210), (3330), (0110) and (0123), while the fourth cell cycle is simulated by positional values (3210), (3000), (0110) and (0003) for genes A, B, C and D respectively, as shown in FIG. 6.

Figure 7:
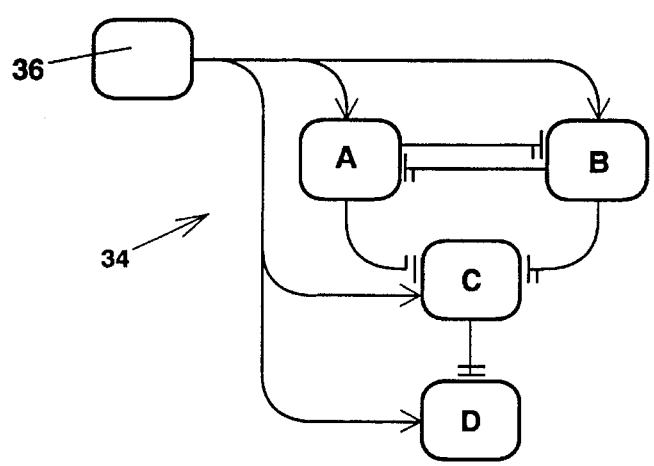
FIG. 7 illustrates another chromatin switching network pursuant to a second generic threshold mechanism associated with growth and development of the embryo shown in FIG. 1.

Another generic threshold mechanism for pattern formation in embryos, characterized as "stripe doubling", is derived from the gene regulation network 34 depicted in FIG. 7, wherein input genes 36 activate genes C and D as well as upstream genes A and B having intermediate repression junctions during a first cell cycle. Repression of gene C by genes A and B according to the network diagrammed in FIG. 7, produces a pattern wherein gene C has gradient concentrations in compartments aligned with the low concentrations of the genes A and B. Such concentrations of gene C are repressed by the higher gradient concentration compartments of genes A and B. As a result of the foregoing, the positional values of the genes A, B, C and D during the first cell cycle are respectively (1210), (0012), (0000) and (0000) from which growth simulation is derived.

During the second cell cycle, gradient concentration bands of the downstream genes C and D within alternate compartments are formed and stabilized for gene C by its autoregulation to inhibit gene D which is thereby repressed to maintain the concentration imposed thereon by gene C located upstream of gene D as diagrammed in FIG. 7. Thus, during the second cell cycle the positional values of the genes A, B, C and D are respectively: (1210), (0012), (1010) and (2222).

During the third and final cell cycle of the second generic mechanism, the gradient concentration pattern for genes A, B and C remain stabilized while the inhibition on the last gene D is lifted to produce therein gradient concentration in compartments alternating with that of gene C so that only the positional values of gene D is altered during the third cell cycle to that of (0202). The foregoing characteristics exhibited by the "stripe doubling" threshold mechanism are also utilized for simulation of Drosophilia embryogenesis based on the technique hereinbefore described and shown in FIG. 6 with respect to the first described generic threshold mechanism.

Based on the foregoing description of the two threshold mechanisms, respectively embodied in the digital gene regulation networks 20 and 34 depicted in FIGS. 5 and 7, the processes of organismal growth and development are approximated for digital simulation reflecting threshold mechanism switching of the genes of chromatin structures representing gene activation between stable states and the biochemical regulatory molecules associated with biochemical events in signal transduction and growth control. The overall process of switching is thereby expressed in terms of Boolean logic dependent on a combination of inputs at a particular time in a cell cycle. The cell cycles are a recurring series of approximated logical switching events which regulate gene expressions. The foregoing referred to switching form steps in cell commitment and differentiation and in organismal development, described as a series of logical statements integrated into a digital program in connection with Drosophilia blastoderm. Such digital simulation program may be run on a computer to simulate growth and development as hereinbefore described with respect to FIGS. 2–7. The foregoing described Boolean logic technique may be similarly utilized to project and simulate growth of Drosophilia nuclei in syncytial blastoderm and provide an overview of temporal and spatial programming of early Drosophilia embryogenesis involving material effect genes, gap genes, terminal genes, pair rule genes and segment polarity genes.

Figure 1:
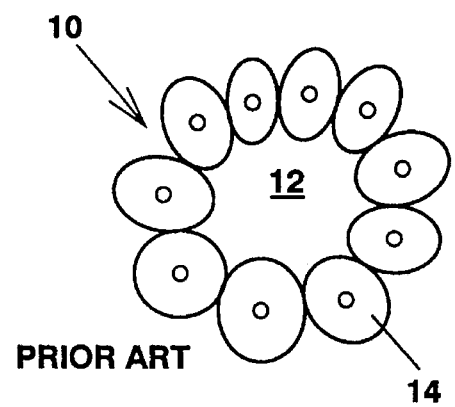
FIG. 1 is a cross-section view of biological organism embryo.
Figure 8:
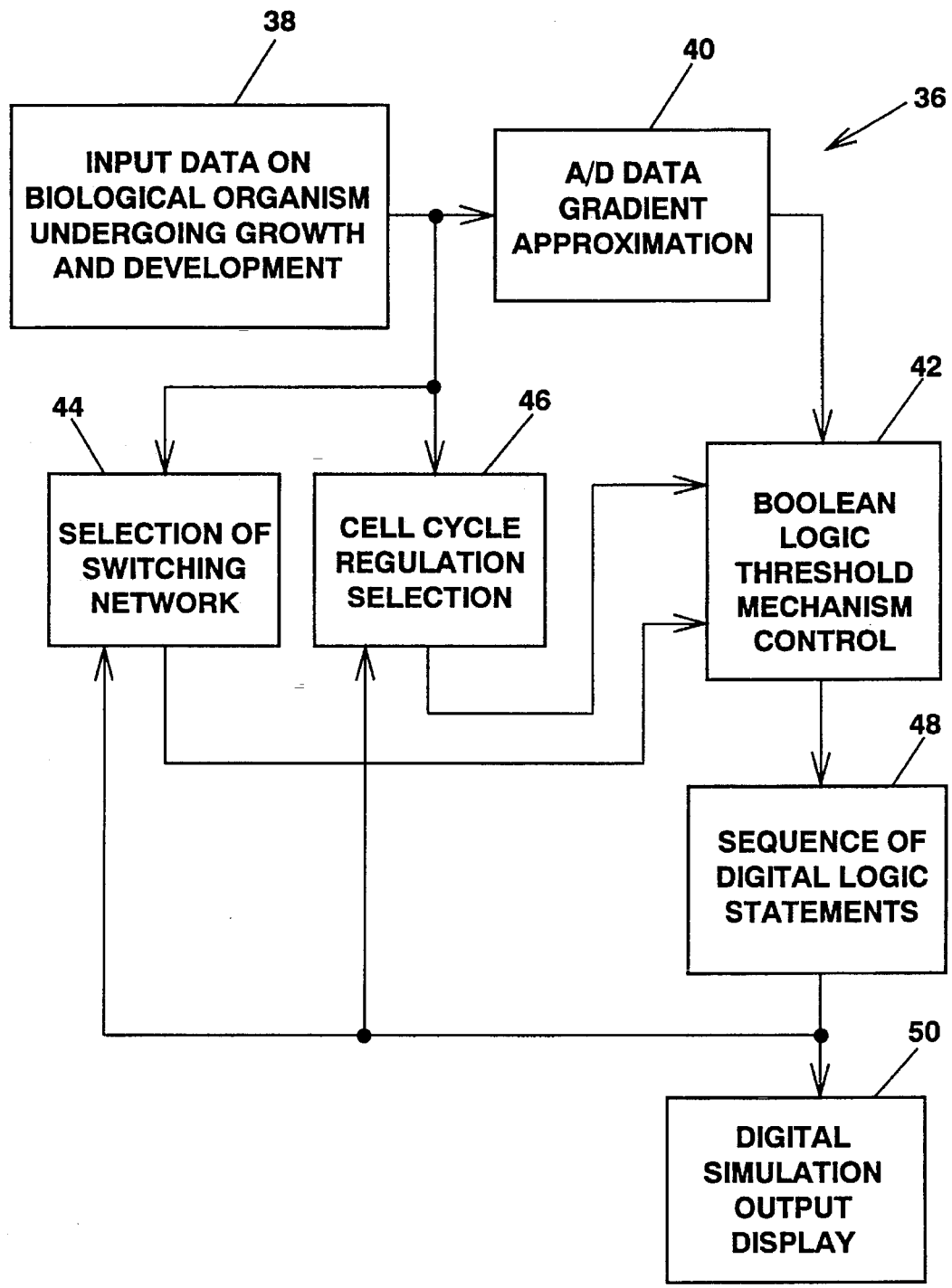
FIG. 8 is a block diagram summarizing the digital simulation method of the present invention.

FIG. 8 diagrams a digital program generally referred to by reference numeral 36, summarizing the biological growth and development simulation method of the present invention as hereinbefore applied by way of example to the Drosophilia embryo 10 shown in FIG. 1. As indicated in FIG. 8, genetic input data on the growth and development of embryo 10, as denoted by block 38, is fed to an analog-to-digital converter for digital approximation of step gradient data as denoted by block 40. Such step gradient data is utilized under Boolean logic control, as denoted by block 42, in accordance with a selected switching network as denoted by block 44, such as the gene switching networks 20 and 34 respectively diagrammed in FIG. 5 and 7. Also, cell cycle regulation is selected, as denoted by block 46, to affect the Boolean logic control 42 through which a cell cycle recurring sequence of digital logic statements are derived, as denoted by block 48. Based on such logic statements, a digital simulation display is obtained as denoted by block 50 in FIG. 8, such as the display shown in FIG. 6 corresponding to the gene selecting network 20 diagrammed in FIG. 5. Other simulation displays dependent on selection of gene switching networks and cell cycle regulation may be obtained through such a program 36, in connection with syncytial blastoderm and early embryogenesis as hereinbefore described as we as to similarly simulate growth and development of the embryos of organisms other than Drosophilia, such as those of a beetle as well as humans and other vertibrates.

Obviously, other modifications and variations of the present invention may be possible in light of the foregoing teachings. It is therefore to be understood that within the scope of the appended claims the invention may be practiced otherwise than as specifically described.

What is claimed is:

1. A method of depicting growth and development of a biological organism from input data generated in response to said organism undergoing molecular and cellular processes, comprising the steps of: converting said input data into a digital format; selecting data thresholds corresponding to the molecular and cellular processes of the biological organism involving gene activation and repression; processing the digital format of the converted input data in accordance with simulation transcription rules under control of the selected data thresholds into a sequence of digital statements; and transforming said sequence of digital statements into a display simulating the growth and development of the biological organism.

2. The method as defined in claim 1 wherein the input data is a continuously varying gradient of regulator concentration within the biological organism while the digital format thereof is a step gradient approximation of said regulator concentration.

3. The method as defined in claim 2 wherein said data thresholds are derived from said molecular and cellular processes described in terms of gene switching and cell cycle regulation.

4. The method as defined in claim 3 wherein said sequence of digital statements is a plurality of positional values extracted by said step of processing as levels of said step gradient approximation in accordance with the simulation transcription rules for arrangement in a multiple series, respectively corresponding to different genes.

5. The method as defined in claim 4 wherein said simulation display graphically diagrams the step gradient levels arranged in formation patterns corresponding to the selected gene switching networks and cell regulation.

6. The method as defined in claim 5 wherein the step gradient levels respectively correspond to various degrees of gene activation and repression.

7. The method as defined in claim 6 wherein said biological organism is a Drosophilia embryo.

8. The method as defined in claim 1 wherein said data thresholds are derived from said molecular and cellular processes described in terms of gene switching and cell cycle regulation.

9. The method as defined in claim 8 wherein said biological organism is a Drosophilia embryo.

10. The method as defined in claim 2 wherein said sequence of digital statements is a plurality of positional values extracted from the gradient approximation by said step of processing in accordance with the simulation transcription rules for arrangement in a multiple series respectively corresponding to different genes.

11. The method as defined in claim 10 wherein levels of the step gradient aproximation respectively correspond to various degrees of gene activation and repression.

12. The method as defined in claim 3 wherein said simulation display graphically diagrams step gradient levels arranged in formation patterns corresponding to the selected gene switching networks and cell regulation.

13. A method of depicting growth and development of a biological organism from input data generated in response to said organism undergoing molecular and cellular processes involving gene activation and repression, comprising the steps of: converting said input data into a digital approximation of regulator concentration; processing said digital approximation under simulation transcription rules into a sequence of digital statements corresponding to various degrees of said gene activation and repression; and transforming said sequence of digital statements into a display simulating the growth and development of the biological organism.

14. The method as defined in claim 13 wherein said sequence of digital statements is a plurality of positional values extracted as levels of a step gradient by said step of processing.

15. The method as defined in claim 14 wherein said simulation display graphically diagrams the levels of the step gradient arranged in formation patterns.

16. In combination with processing of information in accordance with simulation transcription, the rules improvement residing in: a method of depicting growth and development of a biological organism by generating input data in response to said organism undergoing gene activation and repression, comprising the steps of converting said input data into a digital approximation of regulator concentration as the information undergoing said processing in accordance with simulation transcription rules; selecting data thresholds for controlling said processing of the digital approximation to obtain a sequence of digital statements on degrees of said gene activation and repression; and transforming said sequence of digital statements into a display simulating the growth and development of the biological organism.

\* \* \* \* \*